(12) United States Patent
Rosneck et al.

(10) Patent No.: US 8,751,254 B2
(45) Date of Patent: Jun. 10, 2014

(54) METHOD AND APPARATUS FOR MONITORING AND SYSTEMATIZING REHABILITATION DATA

(75) Inventors: James Rosneck, Fairlawn, OH (US); Donald Noe, Cuyahoga Falls, OH (US)

(73) Assignee: Summa Health Systems, Akron, OH (US)

( * ) Notice: Subject to any disclaimer, the term of this patent is extended or adjusted under 35 U.S.C. 154(b) by 1100 days.

(21) Appl. No.: 12/189,257

(22) Filed: Aug. 11, 2008

(65) Prior Publication Data

US 2009/0063194 A1 Mar. 5, 2009

Related U.S. Application Data

(60) Provisional application No. 60/968,140, filed on Aug. 27, 2007.

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC .......... 705/2–3; 600/300, 490, 509, 526, 552; 482/9, 54, 4, 8, 57
See application file for complete search history.

(56) References Cited

U.S. PATENT DOCUMENTS

| | | | | |
|---|---|---|---|---|
| 5,634,467 A | * | 6/1997 | Nevo | 600/490 |
| 5,743,268 A | * | 4/1998 | Kabal | 600/526 |
| 6,259,944 B1 | * | 7/2001 | Margulis et al. | 600/509 |
| 2004/0117214 A1 | * | 6/2004 | Shea | 705/2 |
| 2005/0010117 A1 | | 1/2005 | Agutter et al. | |
| 2005/0032608 A1 | * | 2/2005 | Glusco | 482/9 |
| 2005/0115561 A1 | * | 6/2005 | Stahmann et al. | 128/200.24 |
| 2005/0152836 A1 | * | 7/2005 | Ashley et al. | 424/1.49 |
| 2006/0229506 A1 | * | 10/2006 | Castellanos | 600/300 |
| 2007/0136093 A1 | * | 6/2007 | Rankin et al. | 705/2 |
| 2007/0179349 A1 | * | 8/2007 | Hoyme et al. | 600/300 |
| 2007/0214013 A1 | * | 9/2007 | Silverman | 705/2 |
| 2008/0051261 A1 | * | 2/2008 | Lewis | 482/54 |

FOREIGN PATENT DOCUMENTS

WO WO 2005098467 A2 * 10/2005

* cited by examiner

*Primary Examiner* — Lena Najarian
*Assistant Examiner* — Natalie A Pass
(74) *Attorney, Agent, or Firm* — Roger D. Emerson; Daniel A. Thomson; Emerson Thomson Bennett, LLC

(57) ABSTRACT

A method for tracking an associated patient's progression through rehabilitation includes providing a database, providing a graphic user interface, establishing a functional work capacity for the associated patient, determining a workload based on the functional work capacity, acquiring data from the associated patients' rehabilitation exercises, entering the data into the database, creating a graphical representation of the data, and comparing the data with the workload.

18 Claims, 4 Drawing Sheets

METHOD AND APPARATUS FOR MONITORING AND SYSTEMATIZING REHABILITATION DATA

I. BACKGROUND

This application claims priority to a provisional patent application, Ser. No. 60/968,140, entitled Cardiac Rehab, filed Aug. 27, 2007, which is incorporated by reference. This invention pertains to the art of methods and apparatuses regarding exercise therapy and rehabilitation, and more specifically to apparatuses and methods regarding monitoring and systematizing rehabilitation data.

II. BRIEF DESCRIPTION OF THE DRAWINGS

The invention may take physical form in certain parts and arrangement of parts, at least one embodiment of which will be described in detail in this specification and illustrated in the accompanying drawings which form a part hereof and wherein:

FIG. 2 shows a screen shot of an embodiment of the invention;

FIG. 3 shows a screen shot of an embodiment of the invention; and,

FIG. 4 shows a screen shot of an embodiment of the invention.

III. DEFINITIONS

Figure 1:
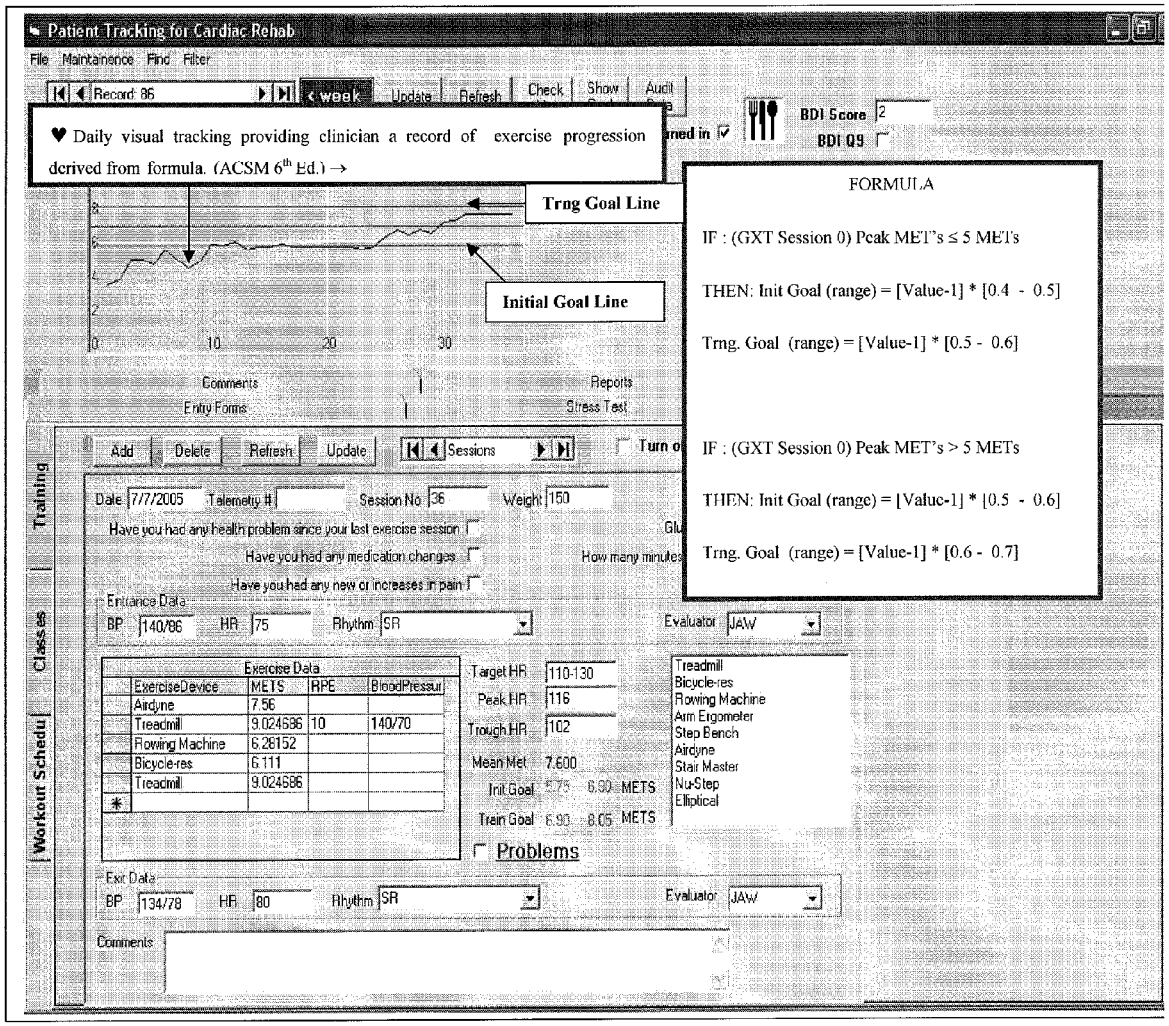
FIG. 1 shows a screen shot of an embodiment of the invention.

Exercise-Workload Intensity (EWI) or Workload (WL)—The estimated oxygen consumption calculated in metabolic equivalents (METs) using regression formula specifically derived for each exercise device.

FWC—Estimated maximal functional work capacity in METs derived via regression formula at volitional peak exertion during a graded exercise test (GXT) (stress test).

Graphical User Interface—a type of user interface which allows people to interact with electronic devices like computers, hand-held devices, household appliances and office equipment.

GXT—graded exercise test. A test that evaluates an individual's physiological response (e.g. heart rate, blood pressure, and oxygen consumption) to exercise, the intensity of which is increased in stages. These tests can be performed using a bench (for step-ups), a cycle ergometer, or a treadmill. A typical test on a treadmill starts with a subject walking gently on a revolving belt, which is accelerated at three minute intervals until the subject is running at maximum pace or until the subject experiences any discomfort or irregularities (e.g. of heartbeat). Heart rate and oxygen consumption are monitored continuously. Blood pressure is measured at rest, during exercise, and after exercise. GXTs provide estimates of the ability of the lungs, heart, and blood vessels to deliver oxygen to respiring tissue; therefore they are measurements of aerobic fitness or cardio-respiratory fitness.

MET—metabolic equivalents, defined as the ratio of a person's working metabolic rate relative to the resting metabolic rate. One MET is defined as 3.5 ml of oxygen per kilogram of body weight per minute and is the oxygen consumption of a person while at complete rest.

IV. DETAILED DESCRIPTION

Cardiac rehabilitation, a service that incorporates patient education, exercise training, and lifestyle modification has been proven to be an effective treatment adjunct for older adult patients with diagnosed cardiac disease. A major component in the rehabilitation of these adult patients is a safe and therapeutically beneficial exercise program tailored to meet the individual baseline physiologic status of the patient and then incrementally adjusted to account for expected changes in functional status. The guidelines for frequency, intensity, and duration of exercise training and the mode of activity recommended by the American Association of Cardiovascular and Pulmonary Rehabilitation (AACVPR), American Heart Association (AHA), and the American College of Sports Medicine (ACSM) for adults with heart disease are subscribed to by the majority of Cardiac Rehab (CR) practitioners throughout the United States.

The ACSM Guidelines for Exercise Testing and Prescription, $6^{th}$ edition advise the mode of training should avoid high-impact activities, and the progression of training should be more gradual in this generally de-conditioned clientele. The prescribed training intensity for the adult cardiac patients is contingent upon their estimated functional work capacity (FWC) in METs established via graded exercise testing (GXT) just prior to program participation. For the purpose of initial exercise prescription and subsequent progression, the ACSM categorizes patients into severe (FWC≤4 METs), moderate (FWC 4 METs-to-8METs), and minimal (FWC>8 METs) impairment groups. For severe patients, it is suggested that exercise work intensity begins at 40% to 50% of the achieved FWC and progress over the ensuing 12 weeks of exercise conditioning to 60%-70% of the initial FWC. For moderate patients, intensity begins at 50% to 60% of the achieved FWC and progress over the ensuing 4-12 weeks of exercise conditioning to 60%-70% of the initial FWC.

Although these clinical guidelines derived from scientific research and enumerated by national governing bodies are present, there is little evidence of uniformity in application of these criteria to actual clinical practice through systematic tracking of patient progression. Most CR programs do not have the ability to track on a daily basis patient workload in METs and those that do generally utilize this data to describe infrequently reported end points rather than ongoing assessment of patient work parameters.

Graphic user interfaces (GUI) have been shown to be an effective tool for tracking progression data in a variety of medical and business settings, as well as serving as a motivational device to increase productivity. The GUI has allowed visual tracking in graphic format by clinical staff and patients of individual daily exercise workloads and has allowed real-time comparisons to exercise intensity goals derived from the ACSM guidelines and visually displayed each time the patient's electronic record is viewed.

Referring now to the drawings wherein the showings are for purposes of illustrating embodiments of the invention only and not for purposes of limiting the same, FIGS. 1-4 show various screen shots of the software program used in the present invention. The software program allows for patient tracking for cardiac rehab, although it is to be understood that this invention is not limited to cardiac rehab, but can be used with any type of patient exercise rehabilitation tracking, chosen with sound medical judgment. The patient tracking uses a GUI to provide detailed information on the patient's exercise rehabilitation.

In this embodiment, a graded exercise test is performed to determine the patient's estimated maximal functional work capacity (FWC) in METs derived via regression formula at volitional peak exertion during a graded exercise test. The types of activities and exercises performed by the patient will vary each day per each patient, as can be seen in FIG. 1 under the table entitled "Exercise Data." If the patient is on the treadmill, the clinician can double mouse click the modality (i.e. treadmill) the patient is currently exercising on, from a selection column to the right of the screen. The modality "treadmill" then automatically drops into the "Exercise Data" column with the estimated WL in METs displayed in a cell to the right. In one embodiment, patients exercise at 5 stations during the 40 minute circuit training session. These 5 estimated WLs are then summed and averaged to arrive at the mean WL for that day. This daily value is then transferred to the MS-Excel line graph to be compared to horizontal goal lines superimposed on the graph.

The data is acquired by indirect measurement via incorporating treadmill speed and elevation estimating METs, by a formula. The formula can be seen on FIG. 1, and, in this embodiment, is as follows:

IF: (GXT Session 0) Peak MET's ≤ 5 METs
THEN: Init Goal (range) = [Value − 1] * [0.4-0.5]
Trng. Goal (range) = [Value − 1] * [0.5-0.6]
IF: (GXT Session 0) Peak MET's > 5 METs
THEN: Init Goal (range) = [Value − 1] * [0.5-0.6]
Trng. Goal (range) = [Value − 1] * [0.6-0.7]

As can be seen in FIG. 1, a graph is derived from the above formula, and provides the clinician a daily visual tracking record of the exercise progression.

As mentioned previously, the American College of Sports Medicine (ACSM) advise that the mode of training should avoid high-impact activities, and the progression of training should be more gradual in this generally de-conditioned coronary artery disease clientele. The prescribed training intensity for the adult cardiac patients is contingent upon their FWC in METs established via GXT just prior to program participation. For the purpose of initial exercise prescription and subsequent progression the ACSM categorizes functional impairment into categories—"severe impairment," "moderate impairment," and "minimal impairment." For patients whose FWC<4 METs it is suggested that exercise work intensity begins at approximately 40% to approximately 50% of the achieved FWC and progress over the ensuing 12 weeks of exercise conditioning to approximately 60%-70% of the initial FWC. For those with FWCs>4 METs intensity begins at approximately 50% to approximately 60% of the achieved FWC and progress over the ensuing 4-12 weeks of exercise conditioning to approximately 60%-70% of the initial FWC. It is to be understood that the present invention is not intended to be limited to the above definitions, but can use any impairment categories chosen using sound medical judgment.

The time duration of the EWI goals will vary per patient given physiologic variables described above. Generally speaking more significantly impaired patients i.e. <4METs will display a more gradual progression slope and plateau into a peak training zone sooner than their more fit counterparts. Some patients who are at FWC's>8 METs will also attend fewer sessions and are therefore accelerated toward training goals sooner. In this embodiment, the EWI goal is determined for each patient as a one-time initial evaluation.

With continuing reference to FIGS. 1-4, the formula provides the initial workload recommendation, and then target workloads are calculated. In this embodiment, the GUI operates in real time to display past and current WLs in graphic format for the clinician, as well as the patient. When changes are made to the patient's WLs, this is immediately reflected in the graphic display. The graphic display uses both 2-dimensional and 3-dimensional displays. A 2-dimensional display is data displayed in graphic and mean numerical values on the same display screen, and a 3-dimensional display is data displayed in graphic, mean numerical values, and individual modality values on the same display screen. In the graphic displays of FIGS. 1-3, the X axis is time in daily sessions and the Y axis is estimated WL in METs.

Figure 2:
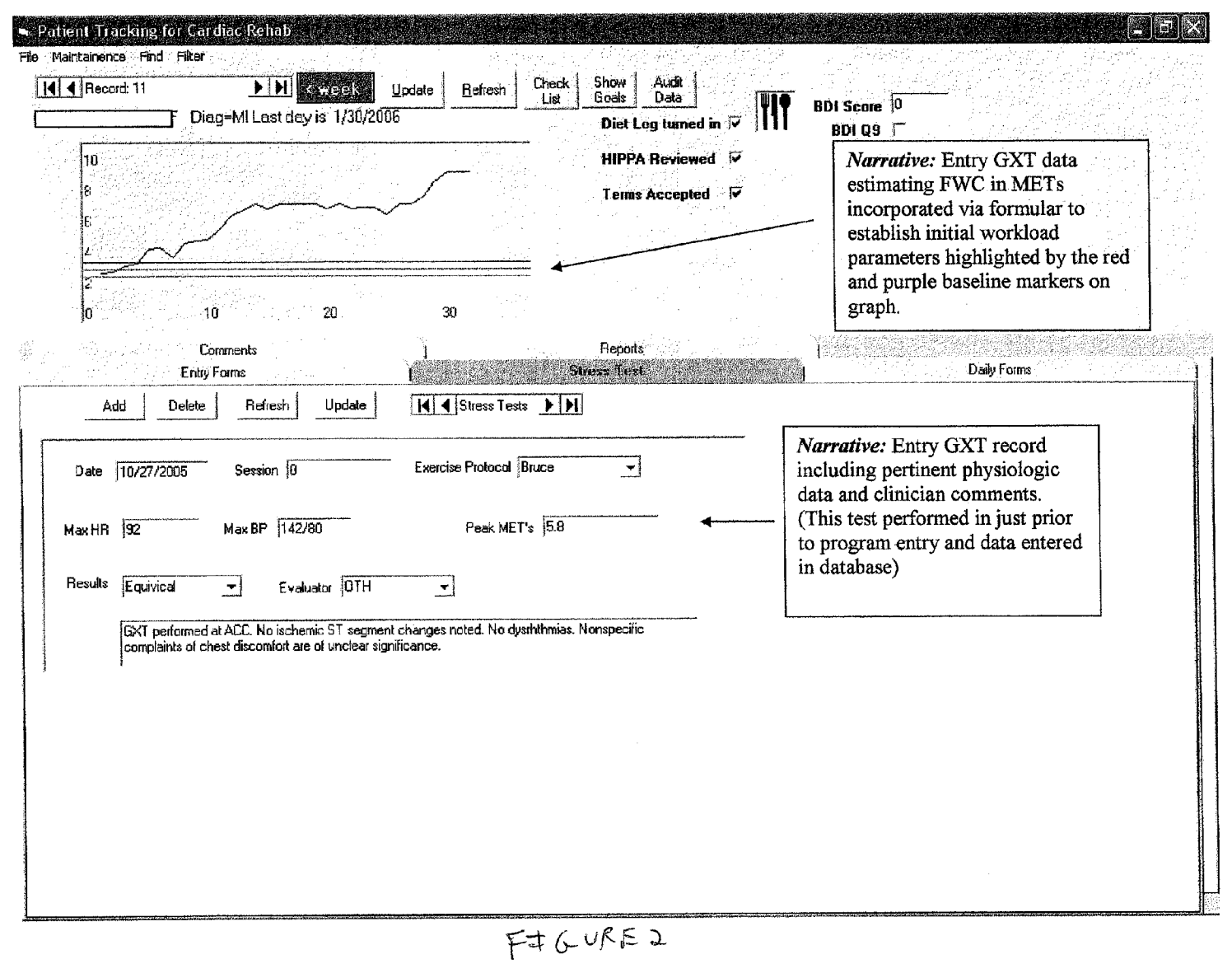
Figure 3:
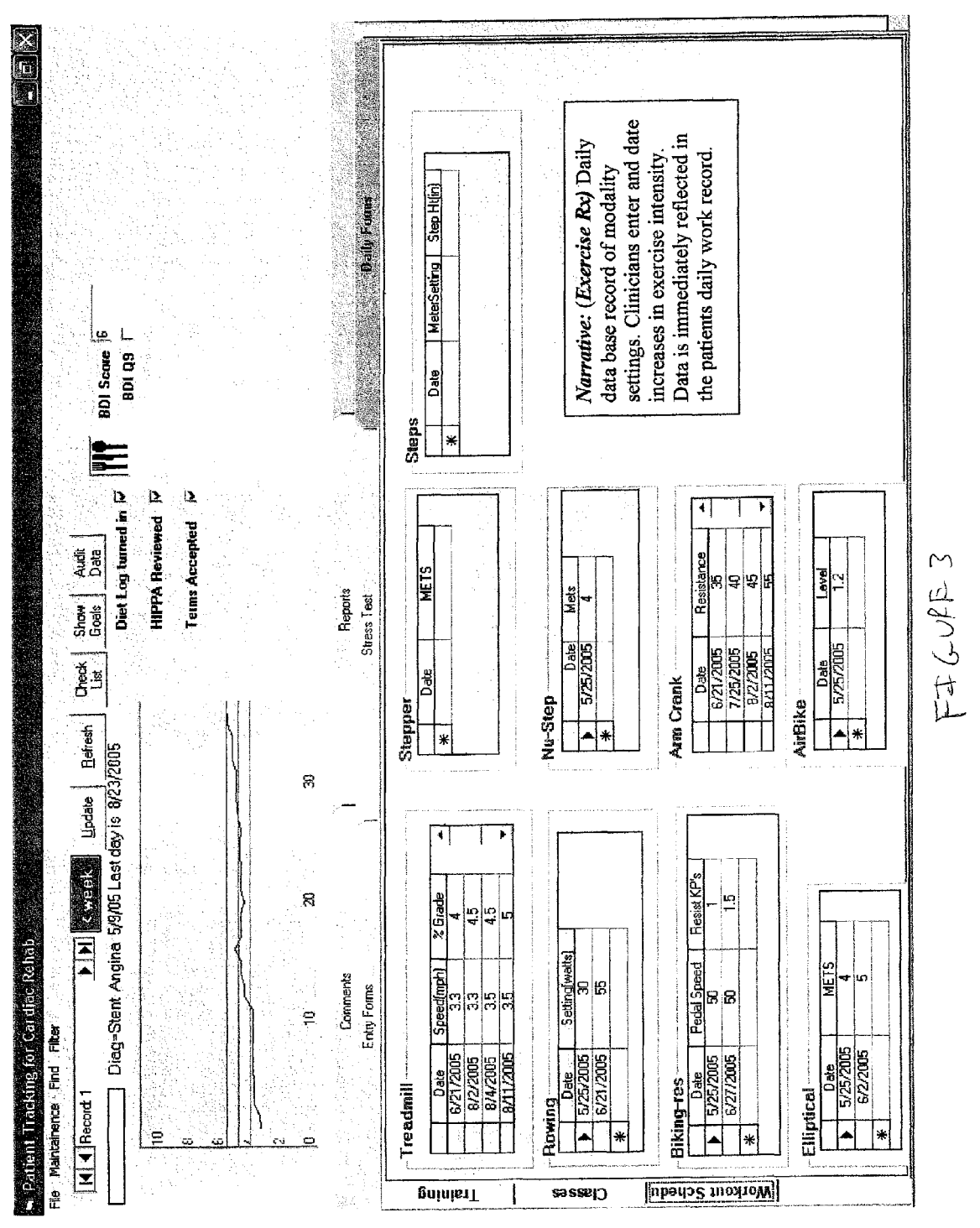
Figure 4:
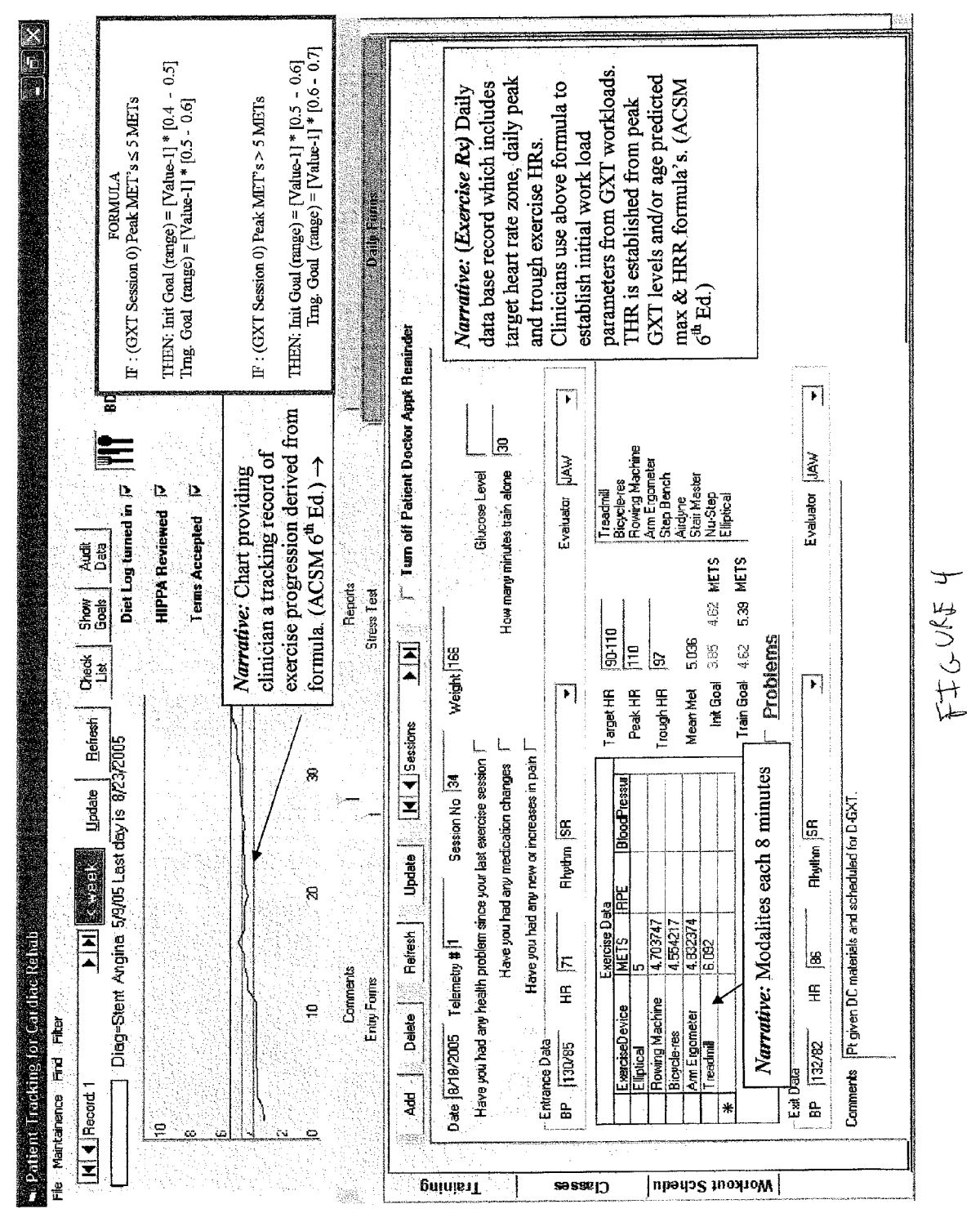

With continued reference to FIGS. 1-4, the graphic display has baseline markers which indicate the initial workload parameters established by the formula, using the GXT data estimating FWC in METs. In one embodiment, the tables have tab options, which display various information regarding the patient. For example, as shown in FIG. 2, a Stress Test tab has GXT entry including pertinent physiologic data and clinician comments. FIGS. 3 and 4 show a Daily Forms tab, which has Training and Workout Schedule tabs. The Training tab, as shown in FIG. 4 shows a daily database record which includes target heart rate zone, daily peak and trough exercise heart rates. Clinicians use the aforementioned formula to establish initial workload parameters and GXT workloads. The target heart rate is established from peak GXT levels and/or age predicted maximums and heart rate formulas.

With continued reference to FIG. 3, the Workout Schedule tab shows a daily database record of modality settings. Clinicians enter and date increases in exercise intensity. Data is immediately reflected in the patient's daily work record.

In this embodiment, each electronic record kept is transferred from VBL format to MS-Access database files. The present invention is directed to displaying the recorded digital comparison (EWI versus EWI goals) at the same time a health-care or medical record is reviewed. This allows for real time evaluation of patient data and the patient's progression.

The embodiments have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

Having thus described the invention, it is now claimed:

We claim:
1. A method for tracking physical work load intensities for an associated patient's progression through cardiovascular and/or pulmonary rehabilitation, the method comprising the steps of:
providing an electronic database, wherein the database assimilates and processes data relevant to comprehensive assessment and therapeutic rehabilitation of adult patients diagnosed with cardiovascular and/or pulmonary disease;
providing an electronic graphic user interface;
performing a graded exercise test to determine the associated patient's peak maximal functional work capacity derived via regression formula at volitional peak exertion;
providing a data entry portal within the database, wherein the data entry portal enables an associated clinician to enter at least one of the following: the patient's functional work capacity peak, maximal work output via the graded exercise test, and cardiopulmonary exercise testing;
electronically determining an initial workload and a training work load goal, based on the functional work capacity;
acquiring electronic data from the associated patients' rehabilitation exercises;
entering the data into the database;

creating an electronic graphical representation of the data, wherein the graphical representation comprises an initial workload goal line and a training exercise goal line;
electronically comparing the data with the initial workload and training work load goal; and
creating an electronic record of the comparison of the data with the work load goal and training work load goal, wherein the functional work capacity is displayed and measured in units of mean metabolic equivalents (METs) per session, and wherein the initial workload goal and training work load goal are calculated using the following formula:

> IF: (GXT Session 0) Peak METs ≤ 5 METs
> THEN: Init Goal (range) = [Value − 1] * [0.4-0.5]
> Trng. Goal (range) = [Value − 1] * [0.5-0.6]
> IF: (GXT Session 0) Peak METs > 5 METs
> THEN: Init Goal (range) = [Value − 1] * [0.5-0.6]
> Trng. Goal (range) = [Value − 1] * [0.6-0.7].

2. The method of claim 1, wherein data comparison is displayed in real time, wherein data entered by an associated clinician is immediately shown in a patient daily work record.

3. The method of claim 2, wherein the graphic user interface comprises at least an X-axis and a Y-axis, wherein the X-axis is a time scale and the Y-axis measures the functional work capacity, wherein the training work load goal, in METs, is entered into the database as horizontal target categories on the electronic graphic user interface.

4. The method of claim 3, wherein the functional work capacity is placed into an associated category, wherein the category is determined by a governing body.

5. The method of claim 4, wherein the method further comprises the step of:
establishing an exercise conditioning goal for the associated patient based upon the functional work capacity.

6. The method of claim 5, wherein the method further comprises the steps of:
creating an electronic record of the graphical representation of the goal and the data.

7. The method of claim 6, wherein the method further comprises the step of:
creating an initial exercise prescription for the associated patient by using the electronic record of the real-time comparison between
i) the patient's real-time functional work capacity, and
ii) at least one corresponding goal.

8. The method of claim 1, wherein the method further comprises the step of:
establishing an exercise conditioning goal for the associated patient based upon the functional work capacity.

9. The method of claim 8, wherein the method further comprises the steps of:
creating an electronic record of the comparison of the data with the work load;
creating an electronic record of the graphical representation of the goal and the data; and,
monitoring patient progress with the electronic graphic use interface.

10. The method of claim 9, wherein the method further comprises the step of:
creating an initial exercise prescription for the associated patient by using the electronic record of the real-time comparison between
i) the patient's real-time functional work capacity, and
ii) at least one corresponding goal.

11. The method of claim 1, wherein the method further comprises:
providing graphical representation of the patient's physiologic data, wherein the data is chosen from the group comprising maximum heart rate, maximum blood pressure, and peak METs; and,
providing graphical representation of modality settings, wherein the modality setting is chosen from associated exercise equipment.

12. The method of claim 1 further comprising the steps of:
in real time, selecting a first exercise modality currently in use by the associated patient;
transferring the selection into a data column, wherein the estimated workload is displayed;
selecting at least a second exercise modality in use by the associated patient subsequent to the use of the first exercise modality, wherein the estimated workload is displayed;
transferring the selection into the data column; and,
summing and averaging the estimated workloads to arrive at a mean workload.

13. The method of claim 1, wherein the step of comparing the data with the workload further comprises the steps of:
comparing real time data from the associated patient to compare the real time data with the initial goal and the training goal;
displaying on the electronic graphic user interface the recorded digital comparison while simultaneously allowing review of an associated medical record.

14. A non-transitory computer readable medium comprising instructions for carrying out a method for tracking physical work load intensities for an associated patient's progression through cardiovascular and/or pulmonary rehabilitation, the instructions comprising the steps of:
providing an electronic database, wherein the database assimilates and processes data relevant to comprehensive assessment and therapeutic rehabilitation of adult patients diagnosed with cardiovascular and/or pulmonary disease;
providing an electronic graphic user interface;
performing a graded exercise test to determine the associated patient's peak maximal functional work capacity derived via regression formula at volitional peak exertion;
providing a data entry portal within the database, wherein the data entry portal enables an associated clinician to enter at least one of the following: the patient's functional work capacity peak, maximal work output via the graded exercise test, and cardiopulmonary exercise testing;
determining an initial workload and a training work load goal, based on the functional work capacity;
acquiring electronic data from the associated patients' rehabilitation exercises;
entering the data into the database;
creating an electronic graphical representation of the data, wherein the graphical representation comprises an initial workload goal line and a training exercise goal line; and,
comparing the data with the initial workload goal and training work load goal; and creating an electronic record of the comparison of the data with the work load goal and training work load goal; wherein the functional work capacity is displayed and measured in units of mean metabolic equivalents (METs) per session, and wherein the initial workload goal and training work load goal are calculated using the following formula:

```
IF: (GXT Session 0) Peak METs ≤ 5 METs
THEN: Init Goal (range) = [Value − 1] * [0.4-0.5]
Trng. Goal (range) = [Value − 1] * [0.5-0.6]
IF: (GXT Session 0) Peak METs > 5 METs
THEN: Init Goal (range) = [Value − 1] * [0.5-0.6]
Trng. Goal (range) = [Value − 1] * [0.6-0.7].
```

15. The computer readable medium of claim 14, wherein data comparison is displayed in real time, wherein data entered by an associated clinician is immediately shown in a patient daily work record.

16. The computer readable medium of claim 15, wherein the graphic user interface comprises at least an X-axis and a Y-axis, wherein the X-axis is a time scale and the Y-axis measures the functional work capacity, wherein the training work load goal, in METs, is entered into the database as horizontal target categories on the electronic graphic user interface.

17. The computer readable medium of claim 16, wherein the functional work capacity is placed into an associated category, wherein the category is determined by a governing body.

18. The computer readable medium of claim 14, wherein the method further comprises the step of:
   establishing an exercise conditioning goal for the associated patient based upon the functional work capacity.

\* \* \* \* \*